(12) United States Patent  (10) Patent No.: US 7,905,922 B2
Bergeron  (45) Date of Patent: Mar. 15, 2011

(54) SURGICAL IMPLANT SUITABLE FOR REPLACEMENT OF AN INTERVERTEBRAL DISC

(75) Inventor: Brian J. Bergeron, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 391 days.

(21) Appl. No.: 11/613,716

(22) Filed: Dec. 20, 2006

(65) Prior Publication Data

US 2008/0154376 A1 Jun. 26, 2008

(51) Int. Cl.
*A61F 2/44* (2006.01)
(52) U.S. Cl. .............. 623/17.16; 623/17.11; 623/17.15
(58) Field of Classification Search ..... 623/17.11–17.16
See application file for complete search history.

(56) References Cited

U.S. PATENT DOCUMENTS

| | | | |
|---|---|---|---|
| 3,567,728 A | 3/1971 | Johnston et al. | |
| 3,867,728 A | * 2/1975 | Stubstad et al. | ........... 623/17.16 |
| 4,309,777 A | 1/1982 | Patil | |
| 4,349,921 A | 9/1982 | Kuntz | |
| 4,759,766 A | 7/1988 | Buettner-Janz | |
| 4,759,769 A | 7/1988 | Hedmann et al. | |
| 4,772,287 A | 9/1988 | Ray et al. | |
| 4,863,477 A | 9/1989 | Monson | |
| 4,911,718 A | 3/1990 | Lee et al. | |
| 4,932,975 A | 6/1990 | Main et al. | |
| 4,946,378 A | 8/1990 | Hirayama et al. | |
| 5,047,055 A | 9/1991 | Bao et al. | |
| 5,071,437 A | 12/1991 | Steffee | |
| 5,108,438 A | 4/1992 | Stone | |
| 5,123,926 A | 6/1992 | Pisharodi | |
| 5,171,281 A | 12/1992 | Parsons et al. | |
| 5,192,326 A | 3/1993 | Bao et al. | |
| 5,192,327 A | 3/1993 | Brantigan | |
| 5,246,458 A | 9/1993 | Graham | |
| 5,258,031 A | 11/1993 | Salib et al. | |
| 5,306,307 A | 4/1994 | Senter et al. | |
| 5,306,309 A | 4/1994 | Wagner et al. | |
| 5,314,477 A | 5/1994 | Marnay | |
| 5,320,644 A | 6/1994 | Baumgartner | |

(Continued)

FOREIGN PATENT DOCUMENTS

FR  2799638  4/2001

(Continued)

OTHER PUBLICATIONS

International Search Report in International Patent Application No. PCT/US02/41425 mailed May 23, 2003.

(Continued)

*Primary Examiner* — Thomas C Barrett
*Assistant Examiner* — Matthew Lawson
(74) *Attorney, Agent, or Firm* — Sprinkle IP Law Group

(57) ABSTRACT

An implant (10) is provided for replacement of an intervertebral disc (14). The implant 10 includes a core portion (20) extending into the disc space (16) and the ligament portion 20 extending longitudinal against the anterior side of the spine (12). The core portion (20) is configured to at least partially replicate the function of an intervertebral disc (14) and the ligament portion (22) is configured to at least partially replicate the function of an anterior longitudinal ligament (28). To this end, the core and ligament portions (20, 22) preferably have different mechanical properties from each other that are customized to provide the particular function desired for each portion (20, 22).

20 Claims, 3 Drawing Sheets

U.S. PATENT DOCUMENTS

| | | | | |
|---|---|---|---|---|
| 5,370,697 | A | 12/1994 | Baumgartner | |
| 5,401,269 | A | 3/1995 | Buettner-Janz et al. | |
| 5,425,773 | A | 6/1995 | Boyd et al. | |
| 5,458,642 | A | 10/1995 | Beer et al. | |
| 5,458,643 | A | 10/1995 | Oka et al. | |
| 5,514,180 | A | 5/1996 | Heggeness et al. | |
| 5,522,899 | A | 6/1996 | Michelson | |
| 5,534,028 | A | 7/1996 | Bao et al. | |
| 5,534,030 | A | 7/1996 | Navarro et al. | |
| 5,549,679 | A | 8/1996 | Kuslich | |
| 5,556,431 | A | 9/1996 | Buettner-Janz | |
| 5,562,738 | A | 10/1996 | Boyd et al. | |
| 5,571,189 | A | 11/1996 | Kuslich | |
| 5,674,294 | A | 10/1997 | Bainville et al. | |
| 5,674,296 | A | 10/1997 | Bryan et al. | |
| 5,676,701 | A | 10/1997 | Yuan et al. | |
| 5,676,702 | A | 10/1997 | Ratron | |
| 5,683,464 | A | 11/1997 | Wagner et al. | |
| 5,683,465 | A | 11/1997 | Shinn et al. | |
| 5,702,450 | A | 12/1997 | Bisserie | |
| 5,755,797 | A | 5/1998 | Baumgartner | |
| 5,782,832 | A | 7/1998 | Larsen et al. | |
| 5,800,549 | A | 9/1998 | Bao et al. | |
| 5,824,093 | A | 10/1998 | Ray et al. | |
| 5,824,094 | A | 10/1998 | Serhan et al. | |
| 5,827,328 | A | 10/1998 | Buttermann | |
| 5,861,041 | A | 1/1999 | Tienboon | |
| 5,865,846 | A | 2/1999 | Bryan et al. | |
| 5,888,220 | A | 3/1999 | Felt et al. | |
| 5,888,226 | A | 3/1999 | Rogozinski | |
| 5,893,889 | A | 4/1999 | Harrington | |
| 5,895,427 | A | 4/1999 | Kuslich et al. | |
| 5,895,428 | A | 4/1999 | Berry | |
| 5,899,941 | A | 5/1999 | Nishijima et al. | |
| 5,961,554 | A | 10/1999 | Janson et al. | |
| 5,964,807 | A | 10/1999 | Gan et al. | |
| 5,976,181 | A | 11/1999 | Whelan et al. | |
| 5,976,186 | A | 11/1999 | Bao et al. | |
| 5,984,967 | A | 11/1999 | Zdeblick et al. | |
| 6,001,130 | A | 12/1999 | Bryan et al. | |
| 6,019,792 | A | 2/2000 | Cauthen | |
| 6,022,376 | A | 2/2000 | Assell et al. | |
| 6,039,763 | A | 3/2000 | Shelokov | |
| 6,093,205 | A * | 7/2000 | McLeod et al. | 623/17.16 |
| 6,110,210 | A * | 8/2000 | Norton et al. | 623/17.16 |
| 6,113,637 | A | 9/2000 | Gill et al. | |
| 6,132,465 | A * | 10/2000 | Ray et al. | 623/17.16 |
| 6,136,031 | A | 10/2000 | Middleton | |
| 6,139,579 | A | 10/2000 | Steffee et al. | |
| 6,146,421 | A | 11/2000 | Gordon et al. | |
| 6,156,067 | A | 12/2000 | Bryan et al. | |
| 6,162,252 | A | 12/2000 | Kuras et al. | |
| 6,165,218 | A | 12/2000 | Husson et al. | |
| 6,179,874 | B1 | 1/2001 | Cauthen | |
| 6,187,048 | B1 | 2/2001 | Milner et al. | |
| 6,206,924 | B1 | 3/2001 | Timm | |
| 6,214,049 | B1 | 4/2001 | Gayer et al. | |
| 6,228,118 | B1 | 5/2001 | Gordon | |
| 6,283,998 | B1 | 9/2001 | Eaton | |
| 6,296,664 | B1 | 10/2001 | Middleton | |
| 6,315,797 | B1 | 11/2001 | Middleton | |
| 6,348,071 | B1 | 2/2002 | Steffee et al. | |
| 6,368,350 | B1 | 4/2002 | Erickson et al. | |
| 6,371,990 | B1 | 4/2002 | Ferree | |
| 6,395,032 | B1 | 5/2002 | Gauchet | |
| 6,395,034 | B1 | 5/2002 | Suddaby | |
| 6,402,784 | B1 | 6/2002 | Wardlaw | |
| 6,402,785 | B1 | 6/2002 | Zdeblick et al. | |
| 6,419,704 | B1 | 7/2002 | Ferree | |
| 6,440,168 | B1 | 8/2002 | Cauthen | |
| 6,468,310 | B1 | 10/2002 | Ralph et al. | |
| 6,478,822 | B1 | 11/2002 | Leroux et al. | |
| 6,482,234 | B1 | 11/2002 | Weber et al. | |
| 6,520,996 | B1 | 2/2003 | Manasas et al. | |
| 6,527,804 | B1 | 3/2003 | Gauchet et al. | |
| 6,527,806 | B2 | 3/2003 | Ralph et al. | |
| 6,576,017 | B2 | 6/2003 | Foley et al. | |
| 6,579,320 | B1 | 6/2003 | Gauchet et al. | |
| 6,582,468 | B1 | 6/2003 | Gauchet et al. | |
| 6,638,310 | B2 | 10/2003 | Lin et al. | |
| 6,652,585 | B2 | 11/2003 | Lange | |
| 6,692,495 | B1 | 2/2004 | Zacouto | |
| 6,712,853 | B2 | 3/2004 | Kuslich | |
| 6,733,531 | B1 | 5/2004 | Trieu | |
| 6,736,850 | B2 | 5/2004 | Davis | |
| 6,878,167 | B2 * | 4/2005 | Ferree | 623/17.16 |
| 7,066,960 | B1 * | 6/2006 | Dickman | 623/17.16 |
| 7,101,400 | B2 | 9/2006 | Thramann et al. | |
| 7,153,325 | B2 * | 12/2006 | Kim et al. | 623/17.15 |
| 7,320,708 | B1 | 1/2008 | Bernstein | |
| 7,326,249 | B2 * | 2/2008 | Lange | 623/17.11 |
| 7,341,601 | B2 * | 3/2008 | Eisermann et al. | 623/17.11 |
| 7,429,270 | B2 * | 9/2008 | Baumgartner et al. | 623/17.12 |
| 2002/0123750 | A1 | 9/2002 | Eisermann et al. | |
| 2002/0128714 | A1 | 9/2002 | Manasas et al. | |
| 2002/0130112 | A1 | 9/2002 | Manasas et al. | |
| 2002/0183848 | A1 * | 12/2002 | Ray et al. | 623/17.12 |
| 2003/0018390 | A1 | 1/2003 | Husson | |
| 2003/0040800 | A1 | 2/2003 | Li et al. | |
| 2003/0045939 | A1 | 3/2003 | Casutt | |
| 2003/0220691 | A1 | 11/2003 | Songer et al. | |
| 2004/0098131 | A1 | 5/2004 | Bryan et al. | |
| 2004/0153160 | A1 | 8/2004 | Carrasco | |
| 2004/0243237 | A1 | 12/2004 | Unwin et al. | |
| 2005/0043733 | A1 * | 2/2005 | Eisermann et al. | 606/61 |
| 2006/0173545 | A1 * | 8/2006 | Cauthen et al. | 623/17.16 |
| 2006/0287730 | A1 * | 12/2006 | Segal et al. | 623/17.16 |
| 2007/0016302 | A1 * | 1/2007 | Dickman | 623/17.13 |
| 2007/0055375 | A1 * | 3/2007 | Ferree | 623/17.11 |
| 2007/0135920 | A1 * | 6/2007 | Ferree | 623/17.11 |
| 2007/0150064 | A1 * | 6/2007 | Ruberte et al. | 623/17.16 |
| 2007/0179621 | A1 * | 8/2007 | McClellan et al. | 623/17.16 |
| 2007/0191956 | A1 * | 8/2007 | Prewett et al. | 623/17.16 |
| 2007/0191957 | A1 * | 8/2007 | Anderson et al. | 623/17.16 |
| 2007/0276494 | A1 * | 11/2007 | Ferree | 623/17.11 |
| 2008/0065218 | A1 * | 3/2008 | O'Neil | 623/17.16 |
| 2008/0077242 | A1 * | 3/2008 | Reo et al. | 623/17.15 |
| 2008/0077244 | A1 * | 3/2008 | Robinson | 623/17.16 |
| 2008/0306593 | A1 * | 12/2008 | McLeod et al. | 623/17.15 |

FOREIGN PATENT DOCUMENTS

| | | |
|---|---|---|
| WO | WO 00/04851 | 2/2000 |
| WO | WO 00/74606 | 12/2000 |
| WO | WO 02/067824 | 9/2002 |
| WO | WO 02/085261 | 10/2002 |
| WO | WO 03/057088 | 7/2003 |

OTHER PUBLICATIONS

Office Action mailed Apr. 7, 2008 in U.S. Appl. No. 11/147,526.
Office Action mailed Apr. 16, 2009 in U.S. Appl. No. 11/147,526.
Office Action mailed Nov. 4, 2008 in U.S. Appl. No. 11/147,526.
The New American Webster Handy College Dictionary, 3rd Edition. Albert and Loy Morehead, 1995, p. 262.
Office Action mailed Dec. 18, 2002 in U.S. Appl. No. 10/035,052.
Office Action mailed Jun. 19, 2003 in U.S. Appl. No. 10/035,052.
Office Action mailed May 27, 2004 in U.S. Appl. No. 10/331,191.
Office Action mailed Nov. 10, 2004 in U.S. Appl. No. 10/331,191.
Office Action mailed Mar. 31, 2005 in U.S. Appl. No. 10/331,191.
Office Action mailed Dec. 20, 2005 in U.S. Appl. No. 10/331,191.
Canadian Office Action mailed May 4, 2009 in Canadian Patent Application No. 2471382.
Australian Office Action mailed Sep. 4, 2007 in Australian Patent Application No. 2002367393.
European Office Action mailed Oct. 10, 2008 in European Patent Application No. 02806230.5.

International Preliminary Report on Patentability mailed Mar. 2, 2004 in International Patent Application No. PCT/US02/41425.
Written Opinion mailed Nov. 12, 2003 in International Patent Application No. PCT/US02/41425.
International Preliminary Report on Patentability issued Dec. 11, 2007 in International Patent Application No. PCT/US06/22178.
International Search Report and Written Opinion mailed Jan. 30, 2007 in International Patent Application No. PCT/US06/22178.
European Office Action mailed Apr. 24, 2009 in European Patent Application No. 06772462.5.
Office Action mailed Nov. 18, 2009 in U.S. Appl. No. 11/147,526.

* cited by examiner

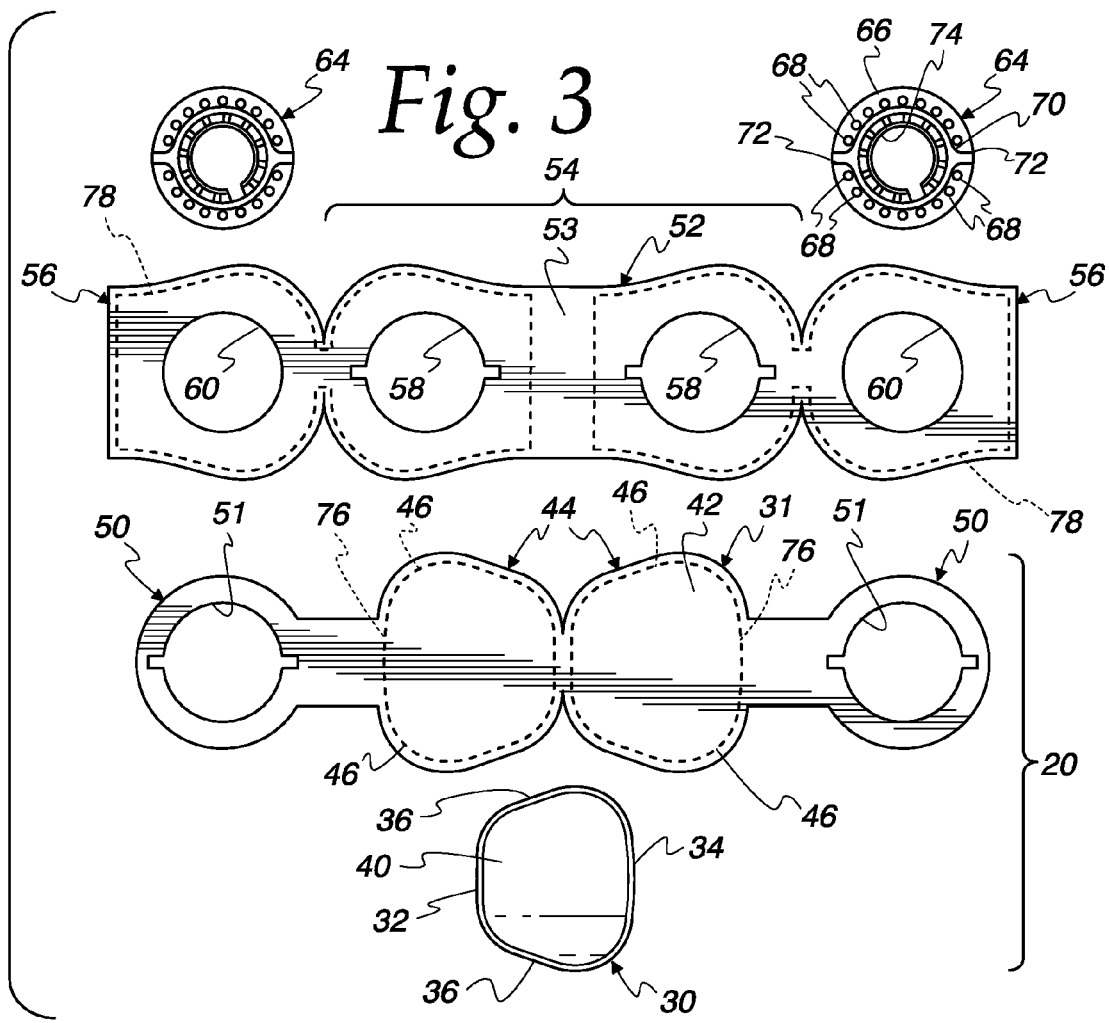
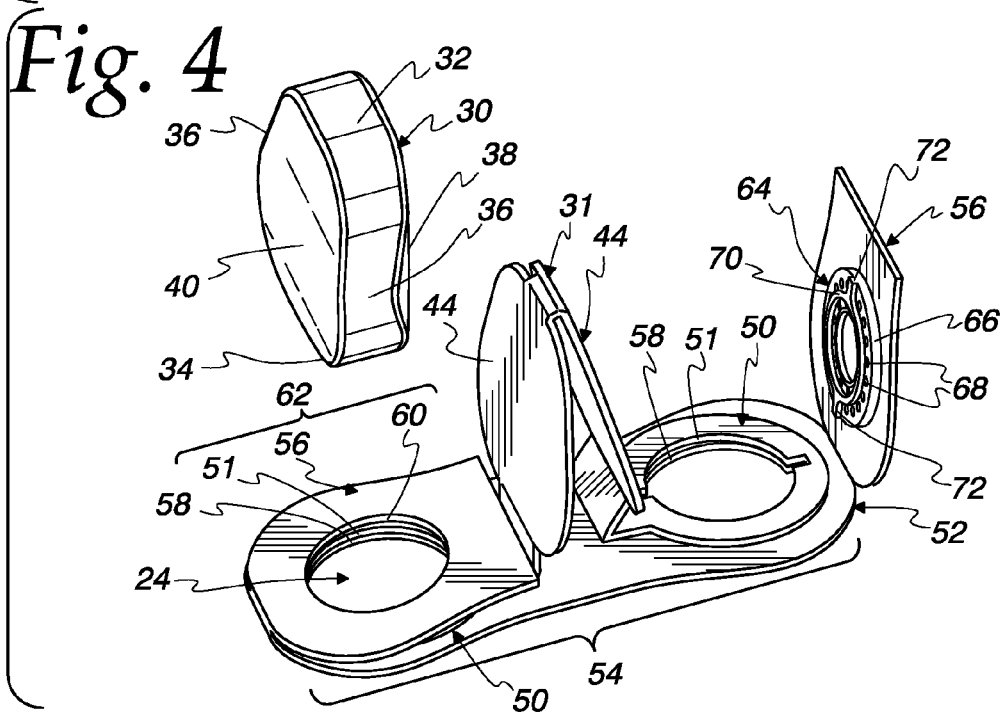

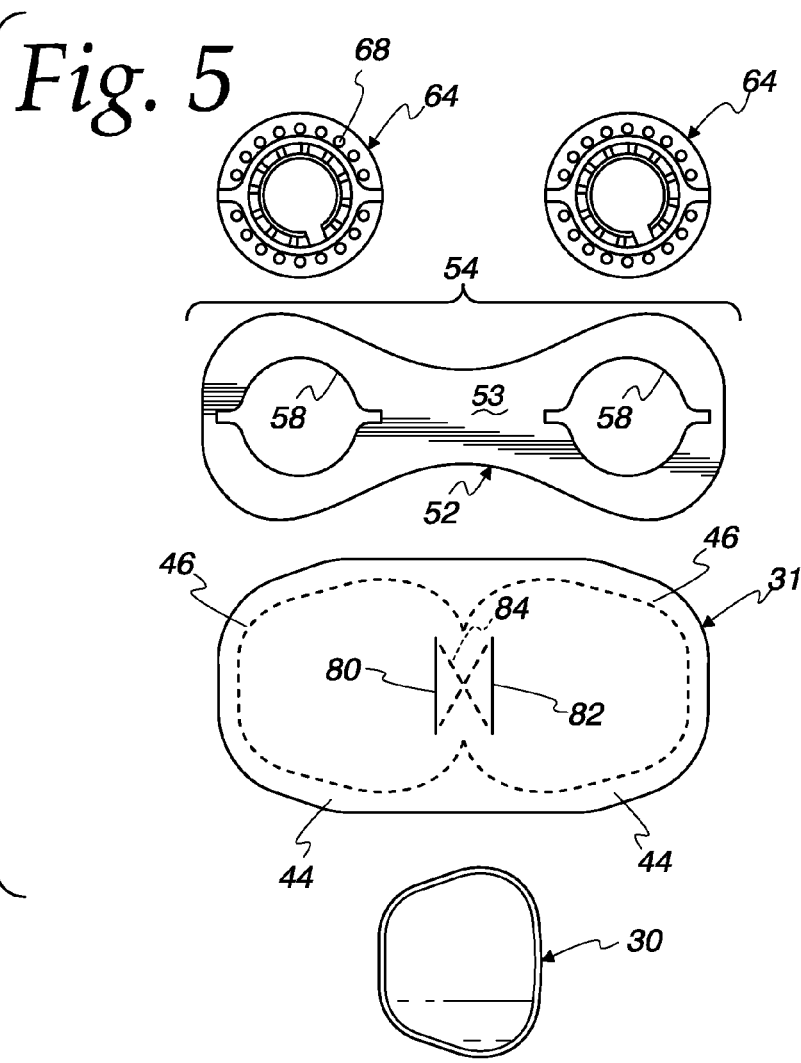
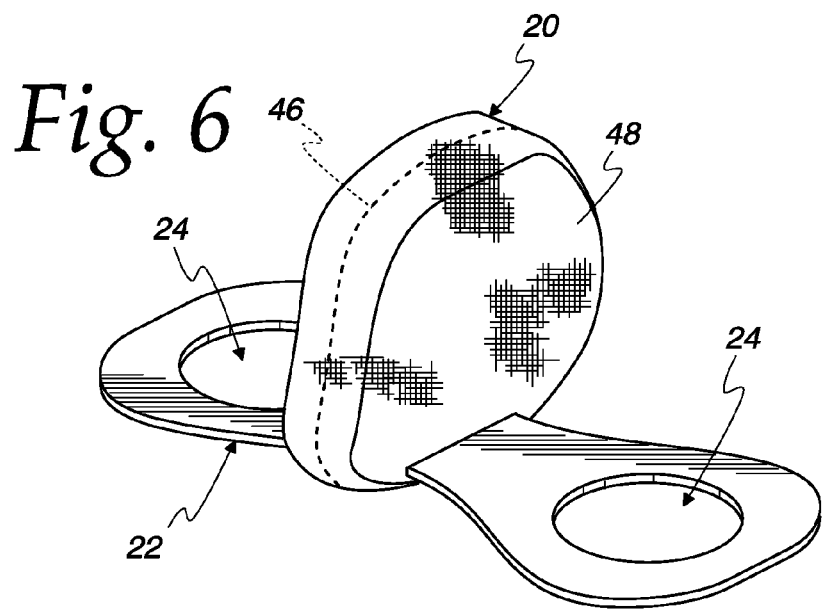

ations, implants that serve as a replacement
SURGICAL IMPLANT SUITABLE FOR REPLACEMENT OF AN INTERVERTEBRAL DISC

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

This invention relates to surgical implants, particularly implants that act as replacements for a joint, and in more particular applications, implants that serve as a replacement for intervertebral disc.

BACKGROUND OF THE INVENTION

Modern surgery often involves the use of implants or prostheses to replace joints in the body. In this regard, implants or prostheses for the replacement of an intervertebral disc are known. One type of such known implants involves the use of metal plates or pads that are attached to the vertebral end plates of the disc space, with the metal pad either being articulating pads or supporting a polymeric spacer between the pads. Such implants can require preparation of the vertebral end plates, and can be sensitive to the positioning of the metal pads on the end plates. Furthermore, such implant may not entirely emulate normal spinal motion, and can introduce a risk that the implant or the spacer may be forced out of the disc space due to abnormal motion of the spine created by the implant.

U.S. Pat. No. 6,093,205 issued Jul. 25, 2000 to McLeod et al (the entire disclosure of which is incorporated herein by reference) discloses another type of implant wherein a core of elastomeric or visco-elastic material is retained within a continuous piece of fabric that forms flanges for attachment to the vertebra adjacent the disc space to retain the core within the disc space. While such a device may be suitable for its intended purpose, there is always room for improvement.

SUMMARY OF THE INVENTION

In accordance with one feature of the invention, an implant is provided for replacement of an intervertebral disc. The implant includes a core portion and a ligament portion. The core portion is configured to at least partially replicate the function of an intervertebral disc, and the ligament portion is configured to at least partially replicate the function of an anterior longitudinal ligament. The core portion includes a resilient core and a first fabric member encasing the resilient core. The ligament portion includes a second fabric member.

According to one feature, the second fabric member is made from a different fabric than the fabric of the first fabric member.

In one feature, the first fabric member includes at least one tab that is sandwiched between two layers of the second fabric member.

As one feature, the fabric of the first fabric member has greater elasticity than the fabric of the second fabric member.

According to one feature, the fabric of the second fabric member has a greater tensile strength than the fabric of the first fabric member.

In one feature, the fabric of the first fabric member has a different weave than the fabric of the second fabric member. As a further feature, the fabric of the first fabric member has a looser weave than the fabric of the second fabric member.

As one feature, the fabric of the first fabric member is made from a different material than the material of the fabric of the second fabric member.

According to one feature, the fabric of the first fabric member is configured to accommodate a desired deformation of the resilient core during compression, and the fabric of the second fabric member is configured to provide a desired resistance to motion of the spine.

In one feature, the first and second fabric members define a layered portion having an opening formed therein for passage of a device to anchor the implant to a vertebra. As a further feature, the implant further includes a grommet in the opening to abut the device. As another feature, the layered portion includes a layer of the first fabric member sandwiched between a pair of layers of the second fabric member.

In accordance with one feature of the invention, a portion of one of the first and second fabric members is sandwiched between a pair of layers of the other of the first and second fabric members to connect the first and second fabric members.

As one feature, another portion of the one of the first and second fabric members is sandwiched between another pair of layers of the other of the first and second fabric members to connect the first and second fabric members.

According to one feature, the one of the first and second fabric members is the first fabric member and the other of the first and second fabric members is the second fabric member.

In one feature, an opening extends through the portion and the two layers to allow passage of a device to anchor the implant to a vertebra.

As one feature, the implant includes a grommet in the opening to abut the device, and the grommet includes a flange sandwiched between the portion and one of the layers of the pair of layers.

In accordance with one feature of the invention, the first fabric member includes a pair of oppositely directed tabs, and the second fabric member includes a pair of end portions, with each of the end portions folded over one the tabs to form a connection between the first and second fabric members.

According to one feature, each of the tabs has an opening therein aligned with a pair of openings in the corresponding end portion. As a further feature, the implant further includes a grommet in the aligned openings, with the grommet sandwiched between one of the tabs and the corresponding end portion.

Other objects, features, and advantages of the invention will become apparent from a review of the entire specification, including the appended claims and drawings.

BRIEF DESCRIPTION OF THE DRAWINGS

FIG. 3 is an exploded plan view of the unassembled components of the implants of FIGS. 1 and 2;

FIG. 4 is a perspective, partially exploded view showing an implant of FIGS. 1-3 in a partially assembled condition;

FIG. 5 is an exploded plan view of the unassembled components of another embodiment of the implants of FIG. 1; and FIG. 6 is a perspective view of the assembled implant of FIG. 5.

DETAILED DESCRIPTION OF THE PREFERRED EMBODIMENT

Figure 1:
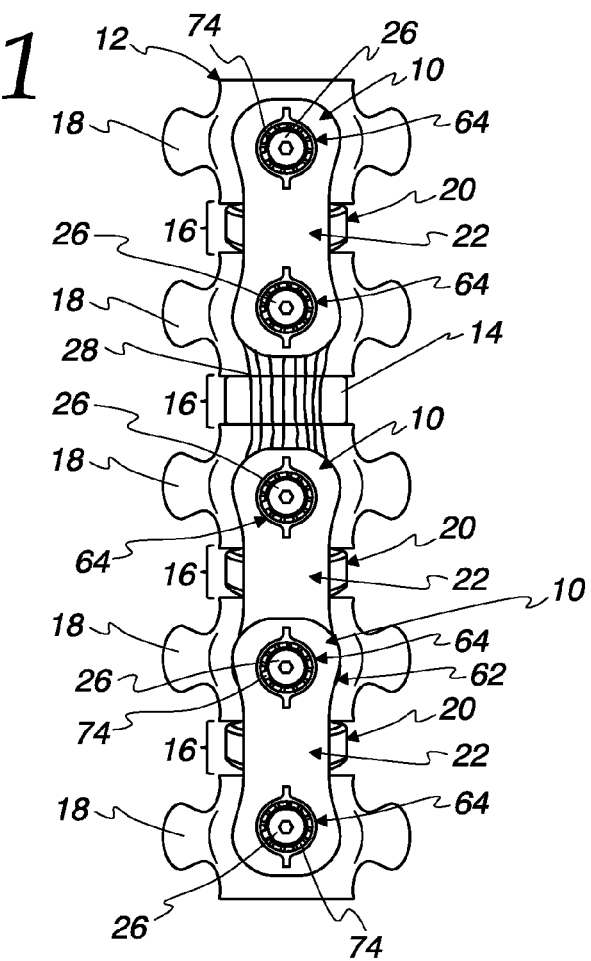
FIG. 1 is a somewhat diagrammatic representation of several spinal implants embodying the present invention and shown in use as viewed from the anterior side of a spine.
Figure 2:
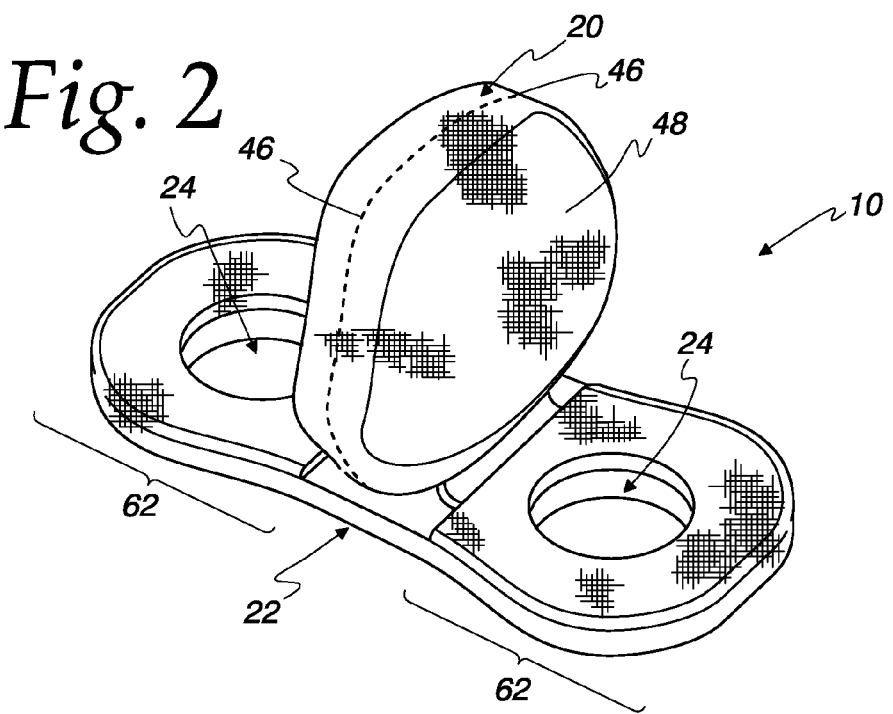
FIG. 2 is a perspective view of one of the implants of FIG. 1.

With reference to FIG. 1, three intervertebral disc implants or prostheses 10 are shown in connection with a spinal column 12 and have replaced the intervertebral disc 14 in three of the disc spaces 16 between the vertebra 18 of the spine 12. The topmost implant 10 illustrates a so-called "single level" replacement, while the bottom two implants 10 illustrate a so-called "multi-level" replacement wherein adjacent intervertebral discs 14 have been replaced. As seen in FIGS. 1 and 2, each of the implants 10 includes a core portion 20 and a ligament portion 22. Each of the implants 10 also includes a pair of attachment openings 24 that receive a device, such as an anchor or bone screw 26 that connects the implant 10 to one of the vertebra 18 with the core portion 20 extending into the disc space 16 and the ligament portion 22 extending longitudinal against the anterior side of the spine 12 in the area normally occupied by the anterior longitudinal ligament 28. In this regard, the core portion 20 is configured to at least partially replicate the function of an intervertebral disc 14 and the ligament portion 22 is configured to at least partially replicate the function of an anterior longitudinal ligament 28. To this end, as will be explained in more detail below, the core and ligament portions 20 and 22 of each implant 10 are laminated to each other to provide a strong connection between the two portions 20 and 22, and preferably, have different mechanical properties from each other that are customized to provide the particular function desired for each portion 20 and 22.

With reference to FIGS. 3 and 4, the core portion 20 includes a resilient core 30 and a fabric member 31. While any desired shape can be used for the core 30, a preferred shape of the core 30 is shown and includes a posterior end 32 that is narrower than an anterior end 34, with symmetric side edges 36 connecting the ends 32 and 34, and contoured upper and lower surfaces 38 and 40 that curve toward each other adjacent the side edges 36 and the ends 32 and 34. The core 30 can be provided in a number of different sizes to provide a correct fit of the implant to the patient's morphology. The core 30 can be made from any suitable resilient material or combination of resilient materials, such as silicon. Preferably, the shape and material selection for the core 30 will allow the core 30 to closely replicate the properties and function of the natural disc 14. The fabric member 31 is preferably made from a continuous piece of fabric 42 and has a pair of core encapsulating portions 44 that can be sewn, stitched or sutured together adjacent their peripheries, as shown schematically by the dashed lines 46, to form a "pillow-case" type enclosure or jacket 48 for the core 30. The fabric member 31 also includes a pair of oppositely directed tab portions 50, with each of the tab portions 50 including an attachment opening 51.

The ligament portion 22 includes a fabric member 52 that is formed from a continuous piece of fabric 53 and includes a central portion 54 and a pair of opposite end portions 56. The central portion 54 includes a pair of attachment openings 58 and each of the end portions 56 includes an attachment opening 60. As best seen in FIG. 4, each of the end portions 56 can be folded over one of the opposite tab portions 50 so that the tab 50 is sandwiched between the end portion 56 and the corresponding part of the central portion 54 to form a layered or laminated connection 62 between the fabric members 31 and 52.

The openings 51, 58 and 60 at each of the connections 62 are aligned to define one of the attachment openings 24. Preferably, the implant 10 also includes a pair of grommets 64 that are located in the openings 24 to abut the anchor or screw devices 26 that attaches the implant 10 to the adjacent vertebra 18. As best seen in FIG. 3, each of the grommets 64 includes an annular flange 66 having an angularly spaced array of suture holes 68, and further includes a short cylindrical wall 70 with a pair of torquing lugs 72 extending radially outwardly therefrom. In the illustrated embodiment, each of the grommets 64 also includes a swivel ring 74 that is retained within an annular groove formed in the cylindrical wall 70. Preferably, the openings 51 and 58 are shaped to accommodate passage of the cylindrical wall 70 and the torquing lug 72 through the tabs 50 and central portion 54, and the flange 66 is preferably sandwiched between the corresponding end portion 56 and tab 50 with sutures extending through selected ones of the holes 68 to attach the grommet 64 to the corresponding end portion 56 before the core portion 20 is attached to the fabric member 52.

The implant 10 is assembled by inserting the core 30 into the enclosure 48 and then closing the enclosure 48 by sewing, stitching, or suturing as indicated schematically by the heavy dashed lines 76 in FIG. 3. As best seen in FIG. 4, the core portion 20 is then placed on top of the central portion 54 and the end portions 56 are folded over the tabs 50, with the walls 70 and lugs 72 of the grommet 64 extending through the aligned openings 51 and 58. Preferably, the laminated connections 62 are then connected at their peripheries by sewing, stitching or suturing, as indicated schematically by the dashed lines 78 in FIG. 3, and by sutures extending through the remaining openings 68 of the grommets 64 and the tabs 50, end portions 56 and central potion 54 that overlay or underlay the flange 66. It should be appreciated that the laminated connections can provide a robust bond or connection between the fabric members 31 and 52.

With reference to FIGS. 5 and 6, another embodiment of the implant 10 is shown wherein the fabric member 31 of the core portion 20 is made from a continuous piece of fabric 42 and has a pair of core encapsulating portions 44 that can be sewn, stitched, or sutured together adjacent the peripheries, as shown schematically by the dashed lines 46, to form a pillowcase type enclosure jacket 48 for the core 30. However, unlike the embodiment of FIGS. 2-4, the fabric member 31 of FIGS. 5 and 6 does not include a pair of oppositely directed tab portions 50. Furthermore, unlike the embodiment of FIGS. 2-4, the fabric member 31 of FIGS. 5-6 includes a pair of slits 80 and 82 that receive the fabric member 52 of the ligament portion 22 when the implant 10 is assembled. In this regard, for the embodiment of FIGS. 5 and 6, the fabric member 52 of the ligament portion 22 is formed from a continuous piece of fabric 53 and includes a central portion 54, but does not include the opposite end portions 56 of FIGS. 2-4. However, the central portion 54 of FIGS. 5-6 does include the attachment openings 58, each adapted to include one of the grommets 64. The implant 10 of FIGS. 5 and 6 is assembled by inserting the fabric member 52 through the slots 80 and 82 and, optionally, by sewing, stitching, or suturing the fabric members 31 and 52 together in any suitable fashion, such as shown for example by the dashed lines 84 in FIG. 5. Next, the core 30 is encapsulated between the portions 44 by sewing, stitching, or suturing the adjacent peripheries, as shown schematically by the dashed lines 46 in FIG. 6. Either before or after the core 30 is encapsulated in the enclosure 48, the grommets 64 are inserted into the openings 58 and sutured to the fabric member 52 through the opening 68 of the grommet 64.

One important advantage of the implant 10 is that it can allow for two different fabrics to be used for the fabric 42 of the fabric member 31 and for the fabric 53 of the fabric member 52. This is desirable because of the different functional and performance requirements for the core portion 20 and the ligament portion 22. For example, the resilient core 30 will tend to expand outwardly when compressed and it may be desirable for the fabric 42 to have sufficient elasticity to accommodate this expansion without overly restraining the core 30. On the other hand, it may be desirable for the fabric 53 of the fabric member 52 to have an increased tensile strength to more closely replicate a ligament. As another example, it may be desirable for the fabric 42 of the fabric member 31 to facilitate tissue growth into the core portion 20, whereas such tissue growth may not be desirable for the ligament portion 22 which may require a fabric 53 that discourages such growth. The desired properties for each fabric member 31 and 52 can be achieved by suitably selecting one or more of the construction details of the fabrics 42 and 53. For example, a looser weave for the fabric 42 may provide the desired elasticity and tissue growth for the fabric member 31 of the core portion 20, while a tighter weave for the fabric 53 may provide an increased tensile strength and/or modulus for the fabric member 52 of the ligament portion 22. Similar results may be achieved by selecting different materials for the fabrics 42 and 53, or by selecting different constructions, such a braid and a knit, for the fabrics 42 and 53. In this regard, it should be understood that any suitable construction and material may be used for the fabrics 42 and 53, including, as a few examples, flat or circular weavings, knitting, embroidery, and/or braiding constructions, and polyester, polypropylene, polyethylene, carbon fiber, glass, glass fiber, polyaramide, metal, copolymers, polylactic acid, polyglycolic acid, silk, biodegradable fibers, silk, cellulosic and polycaprolactone fibers for the materials.

Standard discectomy surgical techniques can be employed to prepare the disc space 16 for the implant 10, wherein the disc 14 and a portion of the anterior longitudinal ligament overlying the disc space 16 are removed. This is followed by distraction of the disc space 16 to restore the appropriate disc height and to liberate the facets. While the distracter is in place, the disc space can be measured for the appropriate size core 30 by inserting a series of differently sized trials to determine the best fit. After the core size is selected, the core portion 20 can be inserted into the disc space 16 and the anchor or bone screws 26 installed while a counter-torque tool engages the lugs 76 to limit or prevent the transfer of torque to the implant through the grommets 64.

Returning to FIG. 1, it should be understood that for the multi-level type replacement shown with the bottom two implants 10, one the attachment openings 24 of one of the implants (the upper implant 10 in FIG. 1) will underlay one of the attachment openings 24 of the other implant 10 and a single anchor or bone screw 26 will extend through the aligned openings 24. Preferably, the opening 24 that underlies the other opening 24 will not have a grommet 64, while the opening of the overlaying opening 24 will have a grommet 64.

It should be appreciated that the implant 10 can closely replicate the functions of the natural disc 14 and the anterior longitudinal ligament 28, with the ligament portion 22 at least partially replicating the functions of the anterior longitudinal ligament 28, the core 30 at least partially replicating the function of the nucleus pulposis of a natural disc, and the jacket 48 at least partially replicating the function of the annulus of a natural disc. In this regard, it should further be appreciated that the ability to utilize a different fabric 42 for the fabric member 31 than the fabric 53 for the fabric member 52 allows for separate optimization of the mechanical properties for the core and ligament portions 20 and 22. It should also be appreciated that the laminated connections 62 can provide a robust bond or connections between the fabric members 31 and 52.

The invention claimed is:

1. An implant for replacement of an intervertebral disc, the implant comprising:
   a core portion and a ligament portion, the core portion configured to at least partially replicate the function of an intervertebral disc, the ligament portion configured to at least partially replicate the function of an anterior longitudinal ligament,
   the core portion comprising a resilient core and a first fabric member having a pair of core encapsulating portions in a first symmetrical configuration for encasing the resilient core,
   the ligament portion comprising a second fabric member having a pair of opposite end portions in a second symmetrical configuration, with each of the end portions including a single attachment opening for passage of a device to anchor the implant to a vertebra,
   wherein the first and second fabric members are made from two separate pieces of different fabric materials, and wherein the first symmetrical configuration is different from the second symmetrical configuration.

2. The implant of claim 1 wherein the first fabric member comprises at least one tab that is sandwiched between two layers of the second fabric member.

3. The implant of claim 1 wherein the fabric of the first fabric member has greater elasticity than the fabric of the second fabric member.

4. The implant of claim 1 wherein the fabric of the second fabric member has a greater tensile strength than the fabric of the first fabric member.

5. The implant of claim 1 wherein the fabric of the first fabric member has a different weave than the fabric of the second fabric member.

6. The implant of claim 5 wherein the fabric of the first fabric member has a looser weave than the fabric of the second fabric member.

7. The implant of claim 1 wherein the fabric of the first fabric member is configured to accommodate a desired deformation of the resilient core during compression, and the fabric of the second fabric member is configured to provide a desired resistance to motion of the spine.

8. The implant of claim 1 wherein the first and second fabric members define a layered portion and wherein the single attachment opening extends through both the first and second fabric members.

9. The implant of claim 8 further comprising a grommet in the opening to abut the device.

10. The implant of claim 8 wherein the layered portion comprises a layer of the first fabric member sandwiched between a pair of layers of the second fabric member.

11. An implant for replacement of an intervertebral disc, the implant comprising:
    a core portion and a ligament portion, the core portion configured to at least partially replicate the function of an intervertebral disc, the ligament portion configured to at least partially replicate the function of a ligament,
    the core portion comprising a resilient core and a first fabric member, wherein the first fabric member com rises a air of core encapsulating portions in a first symmetrical configuration for encasing the resilient core and a pair of end portions in a second symmetrical configuration extending from opposite sides of the pair of core encapsulating portions, and wherein the first symmetrical configuration is different from the second symmetrical configuration, the ligament portion comprising a second fabric member, wherein an each end portion of the first fabric member of the core portion is sandwiched between a pair of layers of the second fabric member of the ligament portion to form a laminated connection between the first and second fabric members, wherein a single attachment opening extends through the laminated connection to provide for passage of a device to anchor the implant to a vertebra, and wherein the first and second fabric members are made from two separate pieces of different fabric materials.

12. The implant of claim 11 further comprising a single attachment opening at the laminated connection.

13. The implant of claim 11 wherein the first fabric member is formed from a continuous piece of fabric-and the second fabric member is formed from a continuous piece of fabric.

14. The implant of claim 11 wherein the single attachment opening extends through the portion of the first fabric member of the core portion and the pair of layers of the second fabric member of the ligament portion to allow passage of a anchor or screw device to anchor the implant to a vertebra.

15. The implant of claim 14 further comprising a grommet in the single attachment opening to abut the anchor or screw device.

16. The implant of claim 15 wherein the grommet includes a flange sandwiched between the portion of the first fabric member of the core portion and one of the pair of layers of the second fabric member of the ligament portion.

17. An implant for replacement of an intervertebral disc, the implant comprising:

a core portion and a ligament portion, the core portion configured to at least partially replicate the function of an intervertebral disc, the ligament portion configured to at least partially replicate the function of a ligament, the core portion comprising a resilient core and a first fabric member having a pair of core encapsulating portions in a first symmetrical configuration for encasing the resilient core, the ligament portion comprising a second fabric member, the first fabric member further comprising a pair of oppositely directed tabs extending from opposite sides of the pair of core encapsulating portions, the second fabric member comprising a pair of end portions in a second symmetrical configuration, each of the end portions of the second fabric member of the ligament portion sandwiches one of the tabs of the first fabric member of the core portion to form a layered connection between the first and second fabric members, wherein a single attachment opening extends through the layered connection to provide for passage of a device to anchor the implant to a vertebra, wherein the first and second fabric members are made from two separate pieces of different fabric materials, and wherein the first symmetrical configuration is different from the second symmetrical configuration.

18. The implant of claim 17 wherein each of the tabs of the first fabric member has an opening therein that is aligned with a pair of openings in the corresponding end portion of the second fabric member to form the single attachment opening.

19. The implant of claim 18 further comprising a grommet in the single attachment opening.

20. The implant of claim 17 wherein the fabric of the first fabric member is configured to accommodate a desired deformation of the resilient core during compression, and the fabric of the second fabric member is configured to provide a desired resistance to motion of the spine.

\* \* \* \* \*